United States Patent
Tabuchi et al.

(10) Patent No.: US 10,941,369 B2
(45) Date of Patent: Mar. 9, 2021

(54) SURFACTANT COMPOSITION

(71) Applicant: KAO CORPORATION, Tokyo (JP)

(72) Inventors: Yukiko Tabuchi, Izumiotsu (JP); Takaya Sakai, Wakayama (JP); Hiroko Endo, Musashino (JP)

(73) Assignee: KAO CORPORATION, Tokyo (JP)

( * ) Notice: Subject to any disclaimer, the term of this patent is extended or adjusted under 35 U.S.C. 154(b) by 18 days.

(21) Appl. No.: 16/324,209

(22) PCT Filed: Aug. 7, 2017

(86) PCT No.: PCT/JP2017/028559
§ 371 (c)(1),
(2) Date: Feb. 8, 2019

(87) PCT Pub. No.: WO2018/030328
PCT Pub. Date: Feb. 15, 2018

(65) Prior Publication Data
US 2019/0169536 A1 Jun. 6, 2019

(30) Foreign Application Priority Data
Aug. 9, 2016 (JP) .............................. JP2016-156777

(51) Int. Cl.
| C11D 1/00 | (2006.01) |
| C11D 1/831 | (2006.01) |
| C11D 1/10 | (2006.01) |
| C11D 1/72 | (2006.01) |
| A61K 8/46 | (2006.01) |
| C11D 1/14 | (2006.01) |
| A61Q 19/10 | (2006.01) |
| A61Q 5/02 | (2006.01) |
| C11D 1/34 | (2006.01) |
| C11D 1/83 | (2006.01) |
| C11D 1/04 | (2006.01) |

(52) U.S. Cl.
CPC ................ *C11D 1/831* (2013.01); *A61K 8/46* (2013.01); *A61Q 5/02* (2013.01); *A61Q 19/10* (2013.01); *C11D 1/04* (2013.01); *C11D 1/10* (2013.01); *C11D 1/14* (2013.01); *C11D 1/143* (2013.01); *C11D 1/146* (2013.01); *C11D 1/34* (2013.01); *C11D 1/345* (2013.01); *C11D 1/72* (2013.01); *C11D 1/83* (2013.01)

(58) Field of Classification Search
None
See application file for complete search history.

(56) References Cited

U.S. PATENT DOCUMENTS

| 3,808,157 A | 4/1974 | Dewitt et al. |
| 4,880,569 A | 11/1989 | Leng et al. |
| 5,078,916 A * | 1/1992 | Kok ........................ C11D 1/143 |
| | | 510/488 |
| 2012/0270764 A1 * | 10/2012 | Brown .................. C07C 309/17 |
| | | 510/427 |
| 2014/0076344 A1 | 3/2014 | Doi et al. |
| 2014/0079658 A1 | 3/2014 | Terazaki et al. |
| 2014/0079660 A1 | 3/2014 | Doi |
| 2015/0202133 A1 | 7/2015 | Doi et al. |
| 2015/0275133 A1 | 10/2015 | Doi |
| 2017/0095410 A1 | 4/2017 | Hara et al. |

FOREIGN PATENT DOCUMENTS

| CN | 105233573 A | 1/2016 |
| CN | 109312278 A | 2/2019 |
| EP | 0 377 261 A2 | 7/1990 |
| EP | 0 482 687 A1 | 4/1992 |
| EP | 3 467 088 A1 | 4/2019 |
| GB | 2 236 538 A | 4/1991 |
| JP | 60-96693 A | 5/1985 |
| JP | 3-126793 A | 5/1991 |
| JP | 2003-81935 A | 3/2003 |
| JP | 2014-76983 A | 5/2014 |
| JP | 2015-27976 A | 2/2015 |
| JP | 2015-27977 A | 2/2015 |
| JP | 2015-178467 A | 10/2015 |
| RU | 2198159 C2 | 2/2003 |
| WO | WO 98/23566 A1 | 6/1998 |
| WO | WO 2017-100051 A2 | 6/2017 |

OTHER PUBLICATIONS

International Search Report for PCT/JP2017/028559 dated Sep. 5, 2017.
International Preliminary Report on Patentability and English translation of the Written Opinion of the International Searching Authority (Forms PCT/IB/338, PCT/IB/373 and PCT/ISA/237) for International Application No. PCT/JP2017/028559, dated Feb. 21, 2019.
Extended European Search Report for European Application No. 17839399.7, dated Mar. 11, 2020.
Chinese Office Action and Search Report for Chinese Application No. 201780048236.4, dated May 6, 2020, with English translation of the Search Report.
English translation of the Russian Search Report, dated Aug. 14, 2020 for Russian Application No. 2019106318.
English translation of the Taiwanese Search Report, dated Nov. 19, 2020, for Taiwanese Patent Application No. 106126839.

\* cited by examiner

*Primary Examiner* — Necholus Ogden, Jr.
(74) *Attorney, Agent, or Firm* — Birch, Stewart, Kolasch & Birch, LLP

(57) ABSTRACT

The present invention provides a surfactant composition which includes a surfactant at a high concentration, while having fluidity over a wide concentration range. A surfactant composition according to the present invention contains the components A, B, C and D described below, and is configured such that: the total content of the components A, B and C is from 30% by mass to 80% by mass (inclusive); the mass ratio of the total content of the components A and B to the content of the component C, namely (A+B)/C is from 20/80 to 80/20; and the mass ratio of the content of the component A to the content of the component B, namely A/B is from 98/2 to 45/55. A: an internal olefin sulfonic acid and/or a salt thereof; B: an anionic surfactant other than the component A; C: a nonionic surfactant; D: water.

6 Claims, No Drawings

SURFACTANT COMPOSITION

TECHNICAL FIELD

The present invention relates to a surfactant composition. More particularly, the present invention relates to a surfactant composition including a high concentration of a surfactant and having fluidity in a wide concentration range.

BACKGROUND ART

Various forms of detergents exist in the market, and liquid detergents are provided for a wide range of cleaning applications such as laundry use, residential use, hair care use, body care use, and the like. Since the liquid detergent has high solubility even during winter season and less worry of an undissolved residue, there is an advantage that such a liquid detergent is easy to use and can exhibit a stably high detergency. Since the liquid detergent can be used in various bottles such as a dispenser and a foaming container, it is also widely applied as a detergent. Due to these advantages, liquid detergents have been growing in the market, and among them, a concentrated liquid detergent which is reduced in size of the detergent itself by blending a high concentration of a surfactant is easier to use because the concentrated liquid detergent can reduce one use amount and becomes a more compact product, which leads to a reduction in container resin amount, transportation cost and energy. Thus, such a concentrated liquid detergent is attracting attention as environment awareness rises.

Patent Document 1 discloses a concentrated liquid detergent composition which can be uniform liquid at a usual storage temperature and comprises a polyalkoxy nonionic surfactant and an ionic surfactant having a non-terminal ionic functional group.

Also, Patent Document 2 discloses a detergent composition excellent in detergency comprising an internal olefin sulfonate having from 8 to 26 carbon atoms, wherein at least 25% by weight of the internal olefin sulfonate has a beta-hydroxyalkane sulfonate structure.

In addition, Patent Document 3 discloses a detergent composition including, as the major components, (i) an anionic surfactant which is an internal olefin sulfonate, a vinylidene sulfonate or a mixture thereof, and (ii) a nonionic surfactant having an HLB value of 10.5 or less, wherein the weight ratio of (i) to (ii) is in the range of 9:1 to 1:9.

In addition, Patent Document 4 discloses a skin or hair cleansing composition which contains an internal olefin sulfonate (A) having 12 to 24 carbon atoms, excellent in foam durability and rinsing property.

In addition, Patent Document 5 discloses a skin or hair cleansing composition containing an internal olefin sulfonate (A) having 12 or more and 24 or less carbon atoms and an anionic surfactant (B) having no sulfate group except for the internal olefin sulfonate (A) and an anionic surfactant having two or more carboxylic acid groups.

Patent Document 6 also discloses a composition containing a sulfonate mixture including an internal olefin sulfonate (A) having 16 carbon atoms and an internal olefin sulfonate (B) having 18 carbon atoms, and at least one foam formation promotor or foam formation enhancer in an aqueous medium.

Further, Patent Document 7 discloses a detergent composition comprising an internal olefin sulfonate having 8 to 26 carbon atoms and at least 25% by weight of f3-hydroxy sulfonate with respect to the total amount of the sulfonate.

PRIOR ART DOCUMENTS

Patent Documents

Patent Document 1: U.S. Pat. No. 4,880,569
Patent Document 2: U.S. Pat. No. 5,078,916
Patent Document 3: JP-A-H3-126793
Patent Document 4: JP-A-2015-27977
Patent Document 5: JP-A-2015-27976
Patent Document 6: JP-A-2015-178467
Patent Document 7: EP-A-0377261

SUMMARY OF THE INVENTION

Problems to be Solved by the Invention

The detergent composition in which a surfactant is blended at a high concentration has an issue to keep solubility of the detergent composition and prevent precipitates or strong gelling, from the point of usability. Therefore, in many liquid detergents, a large amount of organic solvent is used in combination in order to sufficiently dissolve the surfactant and maintain its fluidity.

On the other hand, many organic solvents are petrochemicals, and it is desired to refrain from using organic solvents in view of sustainability, environmental load, safety, and the like. In addition, by providing the fluidity of the detergent with less amount of the organic solvent, it becomes easy to control the foaming properties or viscosity for various uses.

Therefore, there is a demand for a detergent composition capable of uniformly dissolving without gel formation even if a surfactant is blended at a high concentration with less amount of the organic solvent, as well as capable of maintaining fluidity in a wide concentration range without impairing the fluidity even when the concentration is changed by dilution or the like.

However, the technique disclosed in the above patent documents is not sufficient for providing a detergent composition containing a surfactant at a high concentration and maintaining fluidity and low viscosity in a wide concentration range.

The present invention relates to a surfactant composition which includes a high concentration of a surfactant, has fluidity in a wide concentration range.

Means for Solving the Problems

As a result of intensive studies, the present inventors have found that the problems can be solved by a surfactant composition including specific two or more kinds of anionic surfactants and a nonionic surfactant in specific amounts.

The present invention is related to a surfactant composition comprising component A, component B, component C and component D described below,
wherein
a total content of the component A, the component B and the component C is 30% by mass or more and 80% by mass or less;
a mass ratio (A+B)/C of a total content of the component A and the component B to a content of the component C is from 20/80 to 80/20; and
a mass ratio A/B of a content of the component A to a content of the component B is from 98/2 to 45/55, A: an internal olefin sulfonic acid and/or a salt thereof;
B: an anionic surfactant other than the component A;
C: a nonionic surfactant; and
D: water.

Effect of the Invention

According to the present invention, a surfactant composition including a surfactant at a high concentration and having fluidity in a wide concentration range is obtained. Therefore, the amount of an organic solvent to be used in the surfactant composition can be greatly reduced. In addition, the surfactant composition of the present invention is characterized in that fine foams are obtained even when the composition contains the surfactant at a high concentration or even when the composition is diluted, and the composition can sustain a fine foam state for a long time after foaming.

MODE FOR CARRYING OUT THE INVENTION

Hereinafter, the present invention will be described in detail.

A surfactant composition of the present invention includes component A, component B, component C and component D described below,
wherein
a total content of the component A, the component B and the component C is 30% by mass or more and 80% by mass or less;
a mass ratio (A+B)/C of a total content of the component A and the component B to a content of the component C is from 20/80 to 80/20; and
a mass ratio A/B of a content of the component A to a content of the component B is from 98/2 to 45/55,
A: an internal olefin sulfonic acid and/or a salt thereof;
B: an anionic surfactant other than the component A;
C: a nonionic surfactant; and
D: water.

The surfactant composition of the present invention is excellent in fluidity from a high concentration to a low concentration by containing a specific amount of the components A, B and C in a specific content ratio. The reason why such characteristics are developed is not certain but can be thought as follows. The molecular structure of the surfactant is largely distinguished between hydrophilic groups and hydrophobic groups, but in a highly concentrated aqueous surfactant solution, the interaction between the hydrophobic groups is strong, so that liquid crystal formation or solid deposition occurs to cause the increase of viscosity in the aqueous solution. However, it is presumed that by containing a specific amount of the components A, B and C in a specific content ratio, the orientation of the hydrophobic groups is reduced and thus the liquid crystal formation or the solid deposition can be suppressed. However, such action is a presumption and does not restrict the scope of the present invention.

<Component A>

As the internal olefin sulfonic acid and/or the salt thereof, known ones can be used without particular limitation, but from the viewpoint of further improving the effects of the present invention, the internal olefin sulfonic acid and/or the salt thereof has (have) a carbon number of preferably 12 or more, more preferably 14 or more, still more preferably 16 or more, and preferably 24 or less, more preferably 22 or less, still more preferably 20 or less, even still more preferably 18 or less. These may be used singly or two or more kinds thereof having different carbon numbers may be used in combination.

In the present invention, the internal olefin sulfonate is a sulfonate that can be obtained by sulfonating an internal olefin as a raw material (an olefin having a double bond inside the olefin chain), followed by neutralization and hydrolysis. Incidentally, such an internal olefin includes a case where a trace amount of so-called α-olefin in which the double bond exists at the 1-position of the carbon chain is contained. That is, when the internal olefin is sulfonated, β-sultone is produced quantitatively, and a part of β-sultone is changed to γ-sultone and olefin sulfonic acid, and these are then converted into a hydroxyalkane sulfonate and an olefin sulfonate in the neutralization/hydrolysis step (for example, J. Am. Oil Chem. Soc. 69, 39 (1992)). Here, the hydroxy group of the resulting hydroxyalkane sulfonate is within the carbon chain and the double bond of the olefin sulfonate is within the carbon chain. The products obtained are predominantly mixtures of these and some of them include a hydroxyalkane sulfonate having a hydroxy group at the end of the carbon chain or an olefin sulfonate having a double bond at the end of the carbon chain are contained in trace amounts. In the present specification, these respective products and their mixture are collectively referred to as an internal olefin sulfonate. Here, the hydroxyalkane sulfonate is also referred to as a hydroxy form of the internal olefin sulfonate (hereinafter also referred to as HAS) and the olefin sulfonate is also referred to as an olefin form of the internal olefin sulfonate (hereinafter also referred to as IOS). Further, in the present invention, the internal olefin sulfonic acid is an acid state of the internal olefin sulfonate.

Component A is preferably the internal olefin sulfonate. the internal olefin sulfonate is a hydroxyalkane sulfonate, an olefin sulfonate, or a mixture containing them, but is preferably a mixture containing them. In the case of a mixture, the mass ratio (hydroxy form/olefin form) of the content of the hydroxyalkane sulfonate to the content of the olefin sulfonate is preferably 50/50 to 99/1, more preferably 60/40 to 99/1, even more preferably 70/30 to 99/1, still even more preferably 75/25 to 99/1, yet still even more preferably 75/25 to 95/5, from the viewpoint of productivity improvement, and impurity reduction.

The mass ratio of the content of the hydroxyalkane sulfonate to the content of the olefin sulfonate in the component A or the surfactant composition can be determined by separating the hydroxyalkane sulfonate and the olefin sulfonate from the component A or the obtained surfactant composition through HPLC, followed by measurement according to the method described in Examples.

The total content of the hydroxyalkane sulfonate and the olefin sulfonate in the internal olefin sulfonate is 90% by mass or more, preferably 95% by mass or more, still more preferably 98% by mass or more and 100% by mass or less.

From the viewpoint of further improving the effects of the present invention, the internal olefin sulfonic acid and/or the salt thereof preferably contain(s) 5% by mass or more of an internal olefin sulfonic acid and/or a salt thereof having a sulfonic acid group at the 2-position. Also, the internal olefin sulfonic acid and/or the salt thereof preferably contain(s) 40% by mass or less, more preferably 35% by mass or less, even more preferably 30% by mass or less, still even more preferably 28% by mass or less, of an internal olefin sulfonic acid and/or a salt thereof having a sulfonic acid group at the 2-position. Also, the internal olefin sulfonic acid and/or the salt thereof preferably contain(s) 80% by mass or more, more preferably 90% by mass or more, even more preferably 95% by mass or more, still even more preferably 98% by mass or more, and 100% by mass or less, of an internal olefin sulfonic acid and/or a salt thereof having a sulfonic acid group at the 2-position or more.

The internal olefin sulfonic acid and/or the salt thereof can be produced by a known method, for example, by sulfonating, neutralizing, and hydrolyzing an internal olefin. Each step will be specifically described below.

The internal olefin is an olefin having a double bond within the carbon chain. The internal olefin using for a reaction may contain a trace amount of so-called α-olefin in which the double bond is present at the 1-position of the carbon chain.

In order to obtain the internal olefin sulfonic acid and/or the salt thereof, the internal olefin contains an internal olefin having a double bond at the 2-position in an amount of preferably 40% by mass or less, more preferably 35% by mass or less, even more preferably 30% by mass or less, still even more preferably 28% by mass or less, and from the viewpoint of productivity of the internal olefin, the content of such an internal olefin is preferably 10% by mass or more, more preferably 15% by mass or more.

In order to obtain the internal olefin sulfonic acid and/or the salt thereof, the number of carbon atoms of the internal olefin is preferably 12 or more, more preferably 14 or more, even more preferably 16 or more, and is preferably 24 or less, more preferably 22 or less, even more preferably 20 or less, still even more preferably 18 or less.

The internal olefin can be produced by a known method, for example, a method described in WO 2011/052732.

The sulfonation step is not particularly limited, but is a step of reacting the internal olefin with sulfur trioxide to obtain an internal olefin sulfonated product.

The neutralization step is not particularly limited, but is a step of reacting an internal olefin sulfonated product with an alkali compound to obtain a neutralized product.

The hydrolysis step is not particularly limited, but is a step of reacting the resulting neutralized product with water to hydrolyze the neutralized product.

The obtained internal olefin sulfonic acid and/or the salt thereof can be used as it is, but further purification such as desalting and decolorization may be carried out.

<Component B>

As the anionic surfactant other than the component A, known ones can be used without particular limitation. Examples of the anionic surfactant include sulfuric acid ester salts having 10 to 22 carbon atoms, such as alkyl sulfate salt having 10 to 22 carbon atoms, alkenyl sulfate salt having 10 to 22 carbon atoms, polyoxyalkylene alkyl ether sulfate salt having 10 to 22 carbon atoms, polyoxyalkylene alkenyl ether sulfate salt having 10 to 22 carbon atoms, and polyoxyalkylene alkyl phenyl ether sulfate salt having 10 to 22 carbon atoms; sulfonic acid salts having 10 to 22 carbon atoms, such as alkyl sulfosuccinate salt having 10 to 22 carbon atoms, polyoxyalkylene sulfosuccinic acid alkyl ester salt having 10 to 22 carbon atoms, alkanesulfonic acid salt having 10 to 22 carbon atoms, acyl isethionate having 10 to 22 carbon atoms, acyl methyl taurates having 10 to 22 carbon atoms, and alkyl sulfoacetate having 10 to 22 carbon atoms; carboxylic acid salts having 10 to 22 carbon atoms, such as fatty acid salt having 10 to 22 carbon atoms, polyoxyalkylene alkyl ether carboxylate salt having 10 to 22 carbon atoms, polyoxyalkylene alkenyl ether carboxylate salt having 10 to 22 carbon atoms, and polyoxyalkylene alkyl phenyl ether carboxylate salt having 10 to 22 carbon atoms; phosphoric acid ester salts having 10 to 22 carbon atoms, such as alkyl phosphate salt having 10 to 22 carbon atoms and polyoxyalkylene alkyl ether phosphate salt having 10 to 22 carbon atoms; and amino acid salts having an acyl group of 10 to 22 carbon atoms, such as acyl glutamic acid salt, acyl alanine salt, acyl glycine salt, acyl sarcosine salt, and acyl arginine salt. These may be used singly, or two or more of them may be used in combination.

Among the anionic surfactants, from the viewpoint of improving foaming properties of the solution and obtaining fine foam, employed are preferably sulfuric acid ester salts such as alkyl sulfate salt having 10 to 22 carbon atoms and polyoxyalkylene alkyl ether sulfate salt having 10 to 22 carbon atoms; fatty acid salt having 8 to 16 carbon atoms; amino acid salt having an acyl group with 10 to 22 carbon atoms, such as acyl glutamic acid salt, acyl alanine salt, acyl glycine salt, and acyl arginine salt, and more preferably alkyl sulfate salt having 10 to 22 carbon atoms, polyoxyalkylene alkyl ether sulfate salt having 10 to 22 carbon atoms, and fatty acid salt having 8 to 12 carbon atoms.

<Component C>

As the nonionic surfactant, conventional ones can be used without particular limitation. Examples of the nonionic surfactant include polyalkylene glycol type nonionic surfactants such as polyoxyalkylene alkyl ether having 10 to 22 carbon atoms, polyoxyethylene sorbitan fatty acid ester, polyoxyethylene sorbitol fatty acid ester, polyoxyethylene glycerin fatty acid ester, polyoxyethylene fatty acid ester, polyoxyethylene alkylphenyl ether having 10 to 22 carbon atoms, and polyoxyalkylene (hydrogenated) castor oil having 10 to 22 carbon atoms; polyhydric alcohol type nonionic surfactants such as sucrose fatty acid ester, polyglycerin alkyl ether having 10 to 22 carbon atoms, polyglycerin fatty acid ester, alkyl glycoside having 10 to 22 carbon atoms, and acylated alkyl glucamide; and fatty acid alkanol amide. The fatty acid or acyl group of the nonionic surfactant is a fatty acid having 10 to 22 carbon atoms or an acyl group derived therefrom. For example, the fatty acid alkanol amide includes fatty acid monoalkanol amide such as coconut oil fatty acid monoethanolamide and coconut oil fatty acid N-methylmonoethanolamide. These may be used singly or two or more of them may be used in combination.

Among the nonionic surfactants, polyoxyalkylene alkyl ether having 10 to 22 carbon atoms and alkyl glycoside having 10 to 22 carbon atoms are preferably used from the viewpoint of effectively lowering the solution viscosity, and a polyoxyalkylene alkyl ether represented by the following formula (1) is more preferably used.

$$R\text{—}O\text{-}(AO)_n\text{—}H \tag{1}$$

In the above formula, R is a hydrocarbon group having 8 to 22 carbon atoms, AO is an alkyleneoxy group, and n is 5 or more.

The number of carbon atoms of the hydrocarbon group is preferably 10 or more, more preferably 12 or more, and preferably 18 or less, more preferably 16 or less, even more preferably 14 or less, from the viewpoint of effectively lowering the solution viscosity.

The hydrocarbon group may be linear or branched.

Examples of the alkyleneoxy group include an ethyleneoxy group, a propyleneoxy group, a butyleneoxy group, and the like.

The "n" represents an average number of moles of the alkyleneoxy group and is preferably 7 or more, more preferably 10 or more, even more preferably 12 or more, and preferably 100 or less, more preferably 40 or less, even more preferably 30 or less, from the viewpoint of effectively lowering the solution viscosity.

The AO may be one kind of alkyleneoxy group or two or more kinds of alkyleneoxy groups. The AO is preferably one or more kinds selected from an ethyleneoxy group and a propyleneoxy group; more preferably, the AO contains an ethyleneoxy group and a propyleneoxy group; even more preferably, the AO has a block structure comprising an ethyleneoxy group and a propyleneoxy group, from the viewpoint of effectively lowering the solution viscosity.

Examples of the polyoxyalkylene alkyl ether include lauryl ether added with 15 to 25 moles of ethyleneoxy groups, lauryl ether added with a total of 15 to 25 moles of ethyleneoxy groups and propyleneoxy groups, myristyl ether added with 15 to 25 moles of ethyleneoxy groups, myristyl ether added with a total of 15 to 25 moles of ethyleneoxy groups and propyleneoxy groups, cetyl ether added with 15 to 25 moles of ethyleneoxy groups, cetyl ether added with a total of 15 to 25 moles of ethyleneoxy groups and propyleneoxy groups, stearyl ether added with 15 to 25 moles of ethyleneoxy groups, and stearyl ether added with a total of 15 to 25 moles of ethyleneoxy groups and propyleneoxy groups, among which lauryl ether added with 15 to 25 moles of ethyleneoxy groups, lauryl ether added with a total of 15 to 25 moles of ethyleneoxy groups and propyleneoxy groups, myristyl ether added with 15 to 25 moles of ethyleneoxy groups, and myristyl ether added with a total of 15 to 25 moles of ethyleneoxy groups and propyleneoxy groups are preferable, and lauryl ether added with a total of 15 to 25 moles of ethyleneoxy groups and propyleneoxy groups is more preferable.

<Component D>

The component D contained in the surfactant composition of the present invention is water and is not particularly limited, but purified water such as ion-exchange water, distilled water, and reverse osmosis membrane water is preferable.

<Surfactant Composition>

The surfactant composition of the present invention contains at least the components A, B, C, and D.

The total content of the component A, the component B and the component C is 30% by mass or more and 80% by mass or less from the viewpoint of improving the effect of the present invention. From the viewpoint of further improving the effect of the present invention, the total content of the component A, the component B and the component C can be 40% by mass or more, 45% by mass or more, 50% by mass or more, 55% by mass or more, or 60% by mass or more, and can be 75% by mass or less, 70% by mass or less, or 65% by mass or less.

A mass ratio (A+B)/C of a total content of the component A and the component B to a content of the component C is from 20/80 to 80/20. From the viewpoint of further improving the effect of the present invention, the mass ratio (A+B)/C is preferably from 30/70 to 70/30, more preferably from 40/60 to 70/30, even more preferably from 45/55 to 60/40.

A mass ratio A/B of a content of the component A to a content of the component B is from 98/2 to 45/55. From the viewpoint of further improving the effect of the present invention, the mass ratio A/B is preferably from 95/5 to 50/50, more preferably from 95/5 to 70/30, even more preferably from 90/10 to 70/30, still even more preferably from 90/10 to 80/20.

The content of the component A is not particularly limited as long as satisfying the range of the above blending conditions. The content of the component A in the composition may be, for example, 5% by mass or more, 10% by mass or more, 15% by mass or more, 20% by mass or more. Also, the content of the component A may be, for example, 60% by mass or less, 55% by mass or less, 50% by mass or less.

The content of the component B is not particularly limited as long as satisfying the range of the above blending conditions. The content of the component B in the composition may be, for example, 0.2% by mass or more, 1% by mass or more, 5% by mass or more. Also, the content of the component B may be, for example, 30% by mass or less, 25% by mass or less, 20% by mass or less.

The content of the component C is not particularly limited as long as satisfying the range of the above blending conditions. The content of the component C in the composition may be, for example, 5% by mass or more, 10% by mass or more, 15% by mass or more, 20% by mass or more. Also, the content of the component C may be, for example, 60% by mass or less, 50% by mass or less, 40% by mass or less.

The component D, that is, water, can be used in an amount that will be the remaining part of the components A, B, C and other components. The content of the component D in the composition can be 5% by mass or more, 10% by mass or more, 15% by mass or more, 20% by mass or more, 25% by mass or more, 30% by mass or more, 35% by mass or more, or 40% by mass or more, and 70% by mass or less, 65% by mass or less, 60% by mass or less, 55% by mass or less, 50% by mass or less, 45% by mass or less, 40% by mass or less, or 35% by mass or less.

The viscosity at 25° C. of the surfactant composition of the present invention is preferably 3000 mPa·s or less, more preferably 2000 mPa·s or less, even more preferably 1500 mPa·s or less, still even more preferably 1000 mPa·s or less, further preferably 500 mPa·s or less, furthermore preferably 200 mPa·s or less, from the viewpoint of ease of handling. The lower limit of the viscosity at 25° C. is not particularly limited. Here, the viscosity is measured by a tuning fork type vibrational viscometer (VIBRO VISCOMETER SV-10, manufactured by A & D Co., Ltd.) according to the method described in the Examples.

The viscosity at 25° C. may be 0 mPa·s or more. Here, the viscosity of 0 mPa·s includes a case where the viscosity cannot be measured with a tuning fork type vibrational viscometer because the viscosity is too low.

The viscosity at 25° C. may be, for example, 5 mPa·s or more, 10 mPa·s or more, 20 mPa·s or more, 30 mPa·s or more, 40 mPa·s or more, or 50 mPa·s or more.

From the viewpoint of stability of the composition, the surfactant composition of the present invention is homogeneously dissolved preferably at 25° C.

<Other Components>

The surfactant composition of the present invention may optionally contain, in addition to component A, component B, component C and component D, components used in a detergent, such as a surfactant other than component A, component B and component C, a solvent, a perfume, a dye, a preservative, a humectant, an antibacterial agent, an antidandruff agent, a pearling agent, a vitamin agent, a thickener, a pH adjuster, a bleaching agent, a chelating agent, a water-soluble salt, an oil and the like.

Surfactants Other than Component A, Component B and Component C

Examples of the surfactant other than the component A, the component B and the component C include an amphoteric surfactant and a cationic surfactant.

Examples of the amphoteric surfactant include betaine type surfactants such as imidazoline type betaine, alkyldimethylaminoacetic acid betaine, fatty acid amido propyl betaine, and sulfobetaine; amine oxide type surfactants such as alkyldimethylamine oxide; and the like. Specific examples thereof include coconut oil fatty acid amidopropyldimethylcarbobetaine, lauramidopropyl dimethylcarbobetaine, laurylcarboxymethyl hydroxyimidazolium betaine, lauryldimethylaminoacetic acid betaine, laurylhydroxysulfobetaine, and the like. These may be used singly, or two or more of them may be used in combination.

Examples of the cationic surfactant include a quaternary ammonium salt having a hydrocarbon group with 12 to 28 carbon atoms which may be divided with an amide group, an ester group or an ether group; a pyridinium salt; a salt of a tertiary amine with a mineral acid or an organic acid; and the like. Specific examples thereof include mono-long chain alkyltrimethyl ammonium salts such as octyltrimethyl ammonium salt, decyltrimethyl ammonium salt, lauryltrimethyl ammonium salt, myristyltrimethyl ammonium salt, cetyltrimethyl ammonium salt, stearyltrimethyl ammonium salt, behenyltrimethyl ammonium salt, and octadecyloxypropyltrimethyl ammonium salt; di-long chain alkyldimethyl ammonium salts such as dioctyldimethyl ammonium salt, didecyldimethyl ammonium salt, dilauryldimethyl ammonium salt, dimyristyldimethyl ammonium salt, dicetyldimethyl ammonium salt, distearyldimethyl ammonium salt and diisotetradecyldimethyl ammonium salt; and mono-long chain alkyldimethylamine salts such as hydrochloride salts, citrate salts or lactate salts of stearyldimethylamine, behenyldimethylamine, octadecyloxypropyldimethylamine, and dimethylaminopropyl stearic acid amide. These may be used singly, or two or more of them may be used in combination.

Solvent

The surfactant composition of the present invention may contain a solvent for the purpose of improving low temperature stability and cleaning performance. Examples of the solvent include alcohols, glycol ethers, alkylene glycol alkyl ethers and the like. Examples of the alcohol include monohydric alcohols such as ethanol, isopropyl alcohol and butanol; polyhydric alcohols such as ethylene glycol, propylene glycol, butylene glycol, hexylene glycol (2-methyl-2,4-pentanediol), 1,5-pentanediol, 1,6-hexanediol, and glycerin; and aromatic alcohols such as benzyl alcohol. Examples of the alkylene glycol ether include diethylene glycol, triethylene glycol, tetraethylene glycol, dipropylene glycol, and tripropylene glycol. Examples of the alkylene glycol alkyl ether include diethylene glycol monomethyl ether, triethylene glycol monomethyl ether, diethylene glycol monoethyl ether, dipropylene glycol monomethyl ether, dipropylene glycol monoethyl ether, tripropylene glycol monomethyl ether, diethylene glycol monobutyl ether, 1-methoxy-2-propanol, 1-ethoxy-2-propanol, 2-phenoxyethanol, diethylene glycol monophenyl ether, and triethylene glycol monophenyl ether. These may be used singly, or two or more of them may be used in combination.

In the present invention, there is no limitation to inclusion of the solvent, but from the viewpoint of sustainability, environmental load, safety, etc., the content of the solvent in the surfactant composition is preferably 10% by mass or less, more preferably 4% by mass or less, even more preferably 1% by mass or less, still even more preferably 0.1% by mass or less, yet still even more preferably 0% by mass, that is, it is preferred that the surfactant composition does not contain a solvent.

The surfactant composition of the present invention can be prepared by mixing component A, component B, component C, component D and other components.

The order of mixing component A, component B, component C and component D is not particularly limited, and after mixing component A, component B and component C, the mixture may be adjusted to a predetermined concentration by diluting with water, or component A and water may be mixed in advance, component B and water may be premixed, and component C and water may be premixed, and then the three mixed solutions may be mixed. Alternatively, component A and water may be mixed in advance, component B and water may be preliminarily mixed, component C and water may be preliminarily mixed, and such mixed solutions of these may be mixed and diluted with water to adjust to a predetermined concentration.

In the case of preparing a surfactant composition containing other components, there is no particular limitation on the order of preparation, but after preparing a surfactant composition containing, for example, component A, component B, component C and component D, the other components may be blended.

From the viewpoint of obtaining a uniformly dissolved surfactant composition, after mixing the components, the mixture is preferably allowed to store at a predetermined temperature for a predetermined period of time. From the viewpoint of obtaining a uniformly dissolved surfactant composition, the temperature at which the composition is allowed to store is preferably 10° C. or more, more preferably 15° C. or more, even more preferably 20° C. or more, still even more preferably 25° C. or more and from the viewpoint of economic efficiency, the temperature at which the composition is allowed to store is preferably 80° C. or less, more preferably 70° C. or less, even more preferably 60° C. or less, still even more preferably 50° C. or less, yet still even more preferably 40° C. or less, furthermore preferably 30° C. or less. The time to store still depends on the temperature, but is preferably 1 hour or more, more preferably 5 hours or more, even more preferably 12 hours or more, still even more preferably 18 hours or more, furthermore preferably 24 hours or more, even furthermore preferably 2 days or more, still even furthermore preferably 3 days or more, from the viewpoint of sufficiently uniform dissolution, and is preferably 1 month or less, more preferably 20 days or less, even more preferably 10 days or less, from the economical point of view.

The surfactant composition of the present invention contains a surfactant at a high concentration, is excellent in fluidity at from a high concentration to a low concentration, can greatly reduce the amount of organic solvent to be used, and can be suitably used as a liquid detergent. Further, the surfactant composition of the present invention provides fine foams even when the composition contains the surfactant at a high concentration or even when the composition is diluted, and furthermore the composition can sustain a fine foam for a long time after stirring. Accordingly, the composition not only can impart cleaning feeling but also can provide excellent cleaning effect. The surfactant composition of the present invention is used as a detergent, for example, a liquid laundry detergent, a detergent for dishes, a cleaning agent for hair, a cleaning agent for body, a cleaning agent for precision parts, and a cleaning agent for hard surfaces. The surfactant composition of the present invention can be used for each cleaning application by adding to the water and dissolving in water.

The present invention and preferred embodiments of the present invention are described below.

<1>

A surfactant composition comprising component A, component B, component C and component D described below, wherein
a total content of the component A, the component B and the component C is 30% by mass or more and 80% by mass or less;
a mass ratio (A+B)/C of a total content of the component A and the component B to a content of the component C is from 20/80 to 80/20; and
a mass ratio A/B of a content of the component A to a content of the component B is from 98/2 to 45/55,
A: an internal olefin sulfonic acid and/or a salt thereof;
B: an anionic surfactant other than the component A;
C: a nonionic surfactant; and
D: water.

<2>
The surfactant composition according to <1>, wherein the internal olefin sulfonic acid and/or the salt thereof has (have) a carbon number of preferably 12 or more, more preferably 14 or more, still more preferably 16 or more, and preferably 24 or less, more preferably 22 or less, still more preferably 20 or less, even still more preferably 18 or less.

<3>
The surfactant composition according to <1> or <2>, wherein the internal olefin sulfonate includes a hydroxyalkane sulfonate (HAS) and an olefin sulfonate (IOS).

<4>
The surfactant composition according to <3>, wherein the mass ratio (hydroxy form/olefin form) of the content of the hydroxyalkane sulfonate to the content of the olefin sulfonate is preferably 50/50 to 99/1, more preferably 60/40 to 99/1, even more preferably 70/30 to 99/1, still even more preferably 75/25 to 99/1, yet still even more preferably 75/25 to 95/5.

<5>
The surfactant composition according to <3> or <4>, wherein the total content of the hydroxyalkane sulfonate and the olefin sulfonate in the internal olefin sulfonate is 90% by mass or more, preferably 95% by mass or more, still more preferably 98% by mass or more and 100% by mass or less.

<6>
The surfactant composition according to any one of <1> to <5>, wherein the internal olefin sulfonic acid and/or the salt thereof preferably contain(s) 5% by mass or more of an internal olefin sulfonic acid and/or a salt thereof having a sulfonic acid group at the 2-position, and preferably contain(s) 40% by mass or less, more preferably 35% by mass or less, even more preferably 30% by mass or less, still even more preferably 28% by mass or less, of an internal olefin sulfonic acid and/or a salt thereof having a sulfonic acid group at the 2-position.

<7>
The surfactant composition according to any one of <1> to <6>, wherein the internal olefin sulfonic acid and/or the salt thereof preferably contain(s) 80% by mass or more, more preferably 90% by mass or more, even more preferably 95% by mass or more, still even more preferably 98% by mass or more, and 100% by mass or less, of an internal olefin sulfonic acid and/or a salt thereof having a sulfonic acid group at the 2-position or more.

<8>
The surfactant composition according to any one of <1> to <7>, wherein the anionic surfactant is at least one selected from the group consisting of a sulfuric acid ester salt having 10 to 22 carbon atoms, a sulfonate having 10 to 22 carbon atoms, a fatty acid salt having 10 to 22 carbon atoms, a carboxylate having 10 to 22 carbon atoms, a phosphoric acid ester salt having 10 to 22 carbon atoms, and an amino acid salt having an acyl group having 10 to 22 carbon atoms.

<9>
The surfactant composition according to any one of <1> to <8>, wherein the nonionic surfactant is at least one selected from the group consisting of a polyalkylene glycol type nonionic surfactant, a polyhydric alcohol type nonionic surfactant, and a fatty acid alkanol amide.

<10>
The surfactant composition according to <9>, wherein the polyalkylene glycol type nonionic surfactant is a polyoxyalkylene alkyl ether represented by the following formula (1),

$$R\text{—}O\text{-}(AO)_n\text{—}H \quad (1)$$

in the above formula, R is a hydrocarbon group having 8 to 22 carbon atoms, AO is an alkyleneoxy group, and n is 5 or more.

<11>
The surfactant composition according to <10>, wherein the number of carbon atoms of the hydrocarbon group is preferably 10 or more, more preferably 12 or more, and preferably 18 or less, more preferably 16 or less, even more preferably 14 or less.

<12>
The surfactant composition according to <10> or <11>, wherein the "n" represents an average number of moles of the alkyleneoxy group and is preferably 7 or more, more preferably 10 or more, even more preferably 12 or more, and preferably 100 or less, more preferably 40 or less, even more preferably 30 or less.

<13>
The surfactant composition according to any one of <10> to <12>, wherein the AO is preferably one or more kinds selected from an ethyleneoxy group and a propyleneoxy group; more preferably, the AO contains an ethyleneoxy group and a propyleneoxy group; even more preferably, the AO has a block structure comprising an ethyleneoxy group and a propyleneoxy group.

<14>
The surfactant composition according to any one of <10> to <13>, wherein the polyoxyalkylene alkyl ether is preferably lauryl ether added with 15 to 25 moles of ethyleneoxy groups, lauryl ether added with a total of 15 to 25 moles of ethyleneoxy groups and propyleneoxy groups, myristyl ether added with 15 to 25 moles of ethyleneoxy groups, and myristyl ether added with a total of 15 to 25 moles of ethyleneoxy groups and propyleneoxy groups, more preferably lauryl ether added with a total of 15 to 25 moles of ethyleneoxy groups and propyleneoxy groups.

<15>
The surfactant composition according to any one of <1> to <14>, wherein the total content of the component A, the component B and the component C is 30% by mass or more and 80% by mass or less, can be 40% by mass or more, 45% by mass or more, 50% by mass or more, 55% by mass or more, or 60% by mass or more, and can be 75% by mass or less, 70% by mass or less, or 65% by mass or less.

<15-1>
The surfactant composition according to any one of <1> to <14>, wherein the total content of the component A, the component B and the component C is 40% by mass or more.

<15-2>
The surfactant composition according to any one of <1> to <14>, wherein the total content of the component A, the component B and the component C is 55% by mass or more.

<16>
The surfactant composition according to any one of <1> to <15-2>, wherein a mass ratio (A+B)/C of a total content of the component A and the component B to a content of the component C is from 20/80 to 80/20, preferably from 30/70 to 70/30, more preferably from 40/60 to 70/30, even more preferably from 45/55 to 60/40.

<16-1>

The surfactant composition according to any one of <1> to <15-2>, wherein a mass ratio (A+B)/C of a total content of the component A and the component B to a content of the component C is 40/60 or more.

<16-2>

The surfactant composition according to any one of <1> to <15-2>, wherein a mass ratio (A+B)/C of a total content of the component A and the component B to a content of the component C is 45/55 or more.

<16-3>

The surfactant composition according to any one of <1> to <16-2>, wherein a mass ratio (A+B)/C of a total content of the component A and the component B to a content of the component C is 60/40 or less.

<16-4>

The surfactant composition according to any one of <1> to <16-2>, wherein a mass ratio (A+B)/C of a total content of the component A and the component B to a content of the component C is 70/30 or less.

<17>

The surfactant composition according to any one of <1> to <16-4>, wherein a mass ratio A/B of a content of the component A to a content of the component B is from 98/2 to 45/55, preferably from 95/5 to 50/50, more preferably from 95/5 to 70/30, even more preferably from 90/10 to 70/30, still even more preferably from 90/10 to 80/20.

<17-1>

The surfactant composition according to any one of <1> to <16-4>, wherein a mass ratio A/B of a content of the component A to a content of the component B is 70/30 or more.

<17-2>

The surfactant composition according to any one of <1> to <16-4>, wherein a mass ratio A/B of a content of the component A to a content of the component B is from 90/10 to 80/20.

<18>

The surfactant composition according to any one of <1> to <17-2>, wherein the content of the component A in the composition may be 5% by mass or more, 10% by mass or more, 15% by mass or more, 20% by mass or more, and may be 60% by mass or less, 55% by mass or less, 50% by mass or less.

<19>

The surfactant composition according to any one of <1> to <18>, wherein the content of the component B in the composition may be 0.2% by mass or more, 1% by mass or more, 5% by mass or more, and may be 30% by mass or less, 25% by mass or less, 20% by mass or less.

<20>

The surfactant composition according to any one of <1> to <19>, wherein the content of the component C in the composition may be 5% by mass or more, 10% by mass or more, 15% by mass or more, 20% by mass or more, and may be 60% by mass or less, 50% by mass or less, 40% by mass or less.

<21>

The surfactant composition according to any one of <1> to <20>, wherein the content of the component D in the composition can be 5% by mass or more, 10% by mass or more, 15% by mass or more, 20% by mass or more, 25% by mass or more, 30% by mass or more, 35% by mass or more, or 40% by mass or more, and 70% by mass or less, 65% by mass or less, 60% by mass or less, 55% by mass or less, 50% by mass or less, 45% by mass or less, 40% by mass or less, or 35% by mass or less.

<22>

The surfactant composition according to any one of <1> to <21>, wherein the viscosity at 25° C. of the surfactant composition is preferably 3000 mPa·s or less, more preferably 2000 mPa·s or less, even more preferably 1500 mPa·s or less, still even more preferably 1000 mPa·s or less, further preferably 500 mPa·s or less, furthermore preferably 200 mPa·s or less, and may be 0 mPa·s or more, 5 mPa·s or more, 10 mPa·s or more, 20 mPa·s or more, 30 mPa·s or more, 40 mPa·s or more, or 50 mPa·s or more.

<23>

The surfactant composition according to any one of <1> to <22>, wherein the surfactant composition is homogeneously dissolved preferably at 25° C.

<24>

The surfactant composition according to any one of <1> to <23>, wherein the content of the solvent in the surfactant composition is preferably 10% by mass or less, more preferably 4% by mass or less, even more preferably 1% by mass or less, still even more preferably 0.1% by mass or less, yet still even more preferably 0% by mass.

<25>

The surfactant composition according to any one of <1> to <24>, which is a detergent.

<26>

A cleaning method using the surfactant composition according to any one of <1> to <24>.

<27>

Use of the surfactant composition according to any one of <1> to <24> as a detergent.

EXAMPLES

Hereinafter, the present invention will be described specifically based on Examples. Unless otherwise indicated in the table, the content of each component represents percent by mass. Various measurement methods are as follows.

<Measuring Method of Double Bond Position of Internal Olefin>

The double bond position of the internal olefin was measured by gas chromatography (hereinafter abbreviated as GC). Specifically, an internal olefin was reacted with dimethyl disulfide to obtain a dithioated derivative, and then the respective components were separated by GC. The double bond position of the internal olefin was determined from each peak area. The device used for the measurement and the analysis conditions are as follows: a GC device "HP6890" (manufactured by HEWLETT PACKARD), a column "Ultra-Alloy-1HT capillary column" (30 m×250 μm×0.15 μm, manufactured by Frontier Laboratories), a detector (hydrogen flame ion detector (FID)), injection temperature 300° C., detector temperature 350° C., He flow rate 4.6 mL/min.

<Method of Measuring Mass Ratio of Hydroxy Form/Olefin Form>

The mass ratio of the hydroxy form/olefin form of the internal olefin sulfonate was measured by HPLC-MS. Specifically, the hydroxy form and the olefin form were separated by HPLC, and each was identified by applying to MS. As a result, each ratio was determined from the HPLC-MS peak area.

The device and conditions used for the measurement are as follows: HPLC device (trade name: Agilent Technologies 1100, manufactured by Agilent Technologies), column (trade name: L-column ODS 4.6×150 mm, manufactured by Chemicals Evaluation and Research Institute, Japan.), sample preparation (1000-fold dilution with methanol), eluent A (10 mM ammonium acetate added water), eluent B (10 mM ammonium acetate added methanol), gradient (0 minute (A/B=30/70%)→10 minutes (30/70%)→55 minutes (0/100%)→65 minutes (0/100%)→66 minutes (30/70%) →75 minutes (30/70%), MS device (trade name: Agilent Technologies 1100 MS SL (G 1946 D)), MS detection (negative ion detection m/z 60-1600, UV 240 nm).

<Method for Measuring Content of Internal Olefin Contained in Internal Olefin Sulfonate>

The content of the internal olefin contained in the internal olefin sulfonate was measured by GC. Specifically, ethanol and petroleum ether were added to an aqueous solution containing an internal olefin sulfonate, and then extraction was carried out to obtain an internal olefin in the petroleum ether phase. The amount of internal olefin was quantified from the GC peak area. The device used for the measurement and the analysis conditions are as follows: GC device "Agilent Technologies 6850" (manufactured by Agilent Technologies), column "Ultra-Alloy-1HT capillary column" (15 m×250 µm×0.15 µm, manufactured by Frontier Laboratories), detector (hydrogen flame ion detector (FID)), injection temperature 300° C., detector temperature 350° C., and He flow rate 3.8 mL/min.

<Method for Measuring Content of Inorganic Salt Contained in Internal Olefin Sulfonate>

The content of the inorganic salt was measured by potentiometric titration or neutralization titration. Specifically, the content of $Na_2SO_4$ was quantitatively determined by potentiometric titration of sulfate ion ($SO_4^{2-}$). Further, the content of NaOH was quantified by neutralization titration with a dilute hydrochloric acid.

<Measuring Method of Content of Paraffin Component>

The content of the paraffin component was measured by GC. Specifically, ethanol and petroleum ether were added to an aqueous solution containing an internal olefin sulfonate, and then extraction was performed to obtain paraffin in a petroleum ether phase. As a result, the amount of paraffin was quantified from the GC peak area. The device used for the measurement and the analysis conditions are similar to the measurement of the content of the internal olefin in the raw material.

<Method for Measuring Content of Internal Olefin Sulfonate Having Sulfonic Acid Group at 2-Position>

The bonding position of the sulfonic acid group was measured by GC. Specifically, the resulting internal olefin sulfonate was reacted with trimethylsilyldiazomethane to give a methylesterified derivative, and then each component was separated by GC. The content of the internal olefin sulfonate having a sulfonic acid group at the 2-position was calculated using the respective peak area ratios as mass ratios. The device used for the measurement and the analysis conditions are as follows: GC device (trade name: "Agilent Technologies 6850", manufactured by Agilent Technologies), column (trade name: HP-1 capillary column 30 m×320 µm×0.25 µm, manufactured by Agilent Technologies), detector (hydrogen flame ion detector (FID)), injection temperature 300° C., detector temperature 300° C., He flow rate 1.0 mL/min, and oven (60° C. (0 minute)→10° C./minute→300° C. (10 minutes)).

<Measuring Method of Viscosity of Surfactant Composition>

The prepared surfactant composition was allowed to store at room temperature for one day or longer and then the viscosity at 25° C. of the surfactant composition was measured with a tuning fork type vibrational viscometer (VIBRO VISCOMETER SV-10, manufactured by A & D Company Limited.). Continuous measurement was conducted for 3 minutes (data update interval: 5 seconds), and the average value was taken as the viscosity of the surfactant composition. The results are shown in Table 1. In addition, when the viscosity was 12000 mPa·s or more and exceeded the measurement limit of the viscometer, the viscosity was described as "no fluidity".

<Evaluation of Foam Particle Size>

Two grams of the prepared surfactant composition was added to a 10 mL-screw cap test tube (manufactured by Maruem Corporation), and the mixture was stirred for 15 seconds using a pencil mixer (No. 11-229-02, manufactured by AS ONE Corporation). The foam particle size immediately after stirring, 5 minutes after stirring, and 1 hour after stirring was measured using a digital microscope (VHX-1000, manufactured by Keyence Corporation). Specifically, the foam of the solution was gently dropped on a slide glass with a plastic syringe, and this was observed with a digital microscope. Three of the observation images having an average size were visually selected and the respective size was measured to calculate the average value. The results are shown in Table 1. The case where the particle size of the foam particles could not be measured due to the absence of foam particles was marked as x. Also, based on the obtained average value, the foam particle size was evaluated according to the following criteria.

5: The foam particle size is 100 µm or less.
4: The foam particle size is from 101 to 500 µm.
3: The foam particle size is from 501 to 1000 µm.
2: The foam particle size is 1001 µm or more.
1: No foaming at all.

<Production Method of Internal Olefin>

Production Example A

Into a flask equipped with a stirrer, 7000 g (28.9 moles) of 1-hexadecanol (product name: KALCOL 6098, manufactured by Kao Corporation) and 700 g of γ-alumina (STREM Chemicals, Inc.) as a solid acid catalyst (10% by mass relative to the raw material alcohol) were placed, and the reaction was carried out for 5 hours while circulating nitrogen gas (7000 mL/min) into the system at 280° C. with stirring. The alcohol conversion rate after completion of the reaction was 100%, and the purity of C16 internal olefin was 99.7%. The obtained crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 16.5% by mass at C-2 position, 15.4% by mass at C-3 position, 16.4% by mass at C-4 position, 17.2% by mass at C-5 position, 14.2% by mass at C-6 position, and 19.8% by mass at the total of C-7 and C-8 positions.

Production Example B

Into a flask equipped with a stirrer, 7000 g (28.9 moles) of 1-hexadecanol (product name: KALCOL 6098, manufactured by Kao Corporation) and 700 g of γ-alumina (STREM Chemicals, Inc.) as a solid acid catalyst (10% by mass relative to the raw material alcohol) were placed, and the reaction was carried out for 3 hours while circulating nitrogen gas (7000 mL/min) into the system at 280° C. with stirring. The alcohol conversion rate after completion of the reaction was 100%, and the purity of C16 internal olefin was 99.6%. The obtained crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 30.1% by mass at C-2 position, 25.5% by mass at C-3 position, 18.9% by mass at C-4 position, 11.1% by mass at C-5 position, 7.0% by mass at C-6 position, and 7.0% by mass at the total of C-7 and C-8 positions.

Production Example C

Into a flask equipped with a stirrer, 7000 g (25.9 moles) of 1-octadecanol (product name: KALCOL 8098, manufactured by Kao Corporation) and 1050 g of γ-alumina (STREM Chemicals, Inc.) as a solid acid catalyst (15% by mass relative to the raw material alcohol) were placed, and the reaction was carried out for 10 hours while circulating nitrogen gas (7000 mL/min) into the system at 285° C. with stirring. The alcohol conversion rate after completion of the reaction was 100%, and the purity of C18 internal olefin was 98.2%. The obtained crude internal olefin was transferred to a distillation flask and distilled at from 148 to 158° C./0.5 mmHg, whereby 100% pure internal olefin having 18 carbon atoms was obtained. The double bond distribution in the resulting internal olefin was 0.5% by mass at C-1 position, 25.0% by mass at C-2 position, 22.8% by mass at C-3 position, 19.1% by mass at C-4 position, 14.0% by mass at C-5 position, 7.4% by mass at C-6 position, 5.4% by mass at C-7 position, and 5.8% by mass at the total of C-8 and C-9 positions.

<Method for Producing Internal Olefin Sulfonate>

Production Example 1

Sulfonation reaction of the internal olefin having 16 carbon atoms produced in Production Example A was carried out with sulfur trioxide gas having an $SO_3$ concentration of 2.8% by volume using a thin film type sulfonation reactor (inner diameter 14 mmφ, length 4 m) while passing cooling water at 20° C. through an external jacket of the reactor. The reaction molar ratio of $SO_3$/internal olefin was set to 1.09.

The obtained sulfonated product was added to an aqueous alkali solution to which sodium hydroxide was added so as to be 1.2 molar times the theoretical acid value (AV), and neutralized at 30° C. for 1 hour with stirring. The neutralized product was hydrolyzed by heating in an autoclave at 160° C. for 1 hour to obtain a crude product containing a C16 internal olefin sodium sulfonate.

The obtained crude product (300 g) was transferred to a separatory funnel, and 300 mL of ethanol was added thereto. Then, 300 mL of petroleum ether was added per one time to extract and remove oil-soluble impurities. At this time, the inorganic compounds (main ingredient is sodium sulfate) precipitated at the oil/water interface by the addition of ethanol were also separated and removed from the aqueous phase by oil-water separation procedure, and this procedure was carried out three times. The aqueous phase was evaporated to dryness to obtain an internal olefin sodium sulfonate having 16 carbon atoms (A-1). The content of the raw material internal olefin in the obtained internal olefin sodium sulfonate was less than 100 ppm (less than the GC detection lower limit), the content of the inorganic compound was 0.2% by mass, and the content of the paraffin component was 0.2% by mass. In addition, the content of the internal olefin sodium sulfonate in which the sulfonic acid group is present at the 2-position was 9.3% by mass. Further, the content of the hydroxy form (HAS) in the internal olefin sodium sulfonate was 84.2% by mass, and the content of the olefin form (IOS) was 14.4% by mass. The remaining was 1.0% by mass of water.

Production Example 2

Internal olefin sodium sulfonate having 16 carbon atoms (A-2) was obtained under the same conditions as in Production Example 1 except that the internal olefin having 16 carbon atoms produced in Production Example B was used. The content of the raw material internal olefin in the obtained internal olefin sodium sulfonate was less than 100 ppm (less than the GC detection lower limit), the content of the inorganic compound was 0.2% by mass, and the content of the paraffin component was below the detection limit. In addition, the content of the internal olefin sodium sulfonate in which the sulfonic acid group is present at the 2-position was 19.9% by mass. Further, the content of the hydroxy form (HAS) in the internal olefin sodium sulfonate was 83.6% by mass, and the content of the olefin form (IOS) was 15.1% by mass. The remaining was 1.1% by mass of water.

Production Example 3

Internal olefin sodium sulfonate having 18 carbon atoms (A-3) was obtained under the same conditions as in Production Example 1 except that the internal olefin having 18 carbon atoms produced in Production Example C was used. The content of the raw material internal olefin in the obtained internal olefin sodium sulfonate was less than 100 ppm (less than the GC detection lower limit), the content of the inorganic compound was 0.4% by mass, and the content of the paraffin component was below the detection limit. In addition, the content of the internal olefin sodium sulfonate in which the sulfonic acid group is present at the 2-position was 15.0% by mass. Further, the content of the hydroxy form (HAS) in the internal olefin sodium sulfonate was 84.4% by mass, and the content of the olefin form (IOS) was 15.6% by mass.

Production Example 4

Using the internal olefin having 18 carbon atoms produced in Production Example C, the sulfonation reaction was carried out under the same conditions as in Production Example 1, and the obtained sulfonated product was stirred at 60° C. for 1 hour to perform an isomerization reaction. Subsequently, the obtained sulfonated product was added to an alkaline aqueous solution to which sodium hydroxide was added so as to be 1.2 molar times the theoretical acid value (AV), neutralized at 30° C. for 1 hour with stirring, and hydrolyzed and extracted under the same conditions as in Production Example 1 to obtain an internal olefin sodium sulfonate having 18 carbon atoms (A-4). The content of the raw material internal olefin in the obtained internal olefin sodium sulfonate was less than 100 ppm (less than the GC detection lower limit), the content of the inorganic compound was 0.1% by mass, and the content of the paraffin component was below the detection lower limit. In addition, the content of the internal olefin sodium sulfonate in which the sulfonic acid group is present at the 2-position was 15.0% by mass. Further, the content of the hydroxy form (HAS) in the internal olefin sodium sulfonate was 55.1% by mass, and the content of the olefin form (IOS) was 44.9% by mass.

Production Example 5

Using a thin film reactor, sulfur trioxide gas was brought into contact with methyl palmitate to carry out a sulfonation reaction under the condition of a reaction molar ratio (sulfur trioxide gas/methyl palmitate) of 1.2. The obtained sulfonated product was placed in a four-necked flask, aged under heating at 80° C. for 60 minutes, and 5% by mass of methanol was added dropwise to the sulfonated product. The mixture was further aged under heating at 80° C. for 60 minutes to obtain methyl α-sulfopalmitate. This methyl α-sulfopalmitate was put into an aqueous solution of sodium hydroxide and neutralized to pH 6.8 to obtain sodium methyl α-sulfopalmitate (B-5).

<Preparation of Surfactant Composition>

Example 1

The internal olefin sodium sulfonate having 16 carbon atoms (A-1) prepared in Production Example 1, polyoxyalkylene alkyl ether sulfate salt (EMAL 20C, manufactured by Kao Corporation) (B-1), and polyoxyalkylene alkyl ether (C-1) represented by the following formula were taken in a beaker, with the formulation shown in Table 1, and an appropriate amount of water was added thereto. The mixture was warmed to 60° C. and mixed, and then cooled to room temperature to prepare a surfactant composition.

(C-1)

In the formula, C-1 is a compound obtained by a block addition reaction of 9 moles of ethylene oxide, 2 moles of propylene oxide, and 9 moles of ethylene oxide in this order relative to 1 mole of a primary linear alcohol having 10 to 14 carbon atoms derived from coconut oil; R is a linear alkyl group having 10 to 14 carbon atoms; a is 9; b is 2; and c is 9.

Examples 2 to 22 and Comparative Examples 1 to 9

Surfactant compositions were prepared in the same manner as in Example 1 except that the raw materials and formulations shown in Tables 1 to 3 were employed. A-2 to A-4, B-2 to B-8, C-2 and C-3 in Tables 1 to 3 are the following compounds. Further, when B-3, B-6 or B-7 was used, an aqueous solution of sodium hydroxide was mixed so as to be 1 equivalent to B-3, B-6 or B-7.

A-2: Internal olefin sodium sulfonate having 16 carbon atoms prepared in Production Example 2

A-3: Internal olefin sodium sulfonate having 18 carbon atoms prepared in Production Example 3

A-4: Internal olefin sodium sulfonate having 18 carbon atoms prepared in Production Example 4

B-2: Sodium dodecyl sulfate (manufactured by MP Biomedicals, Inc.)

B-3: Lauric acid (LUNAC L-98, manufactured by Kao Corporation)

B-4: Di(2-ethylhexyl) sodium sulfosuccinate (manufactured by Wako Pure Chemical Industries, Ltd.)

B-5: Sodium methyl α-sulfopalmitate produced in Production Example 5

B-6: Polyoxyethylene dodecyl ether carboxylic acid (AKYPO LM-26C, manufactured by Kao Chemicals GmbH)

B-7: N-Lauroyl glutamic acid (AMISOFT LA-D, manufactured by Ajinomoto Co., Ltd.)

B-8: Sodium N-lauroylsarcosinate (manufactured by Wako Pure Chemical Industries, Ltd.)

C-2: Lauryl glycoside (MAIDOLE 12, manufactured by Kao Corporation)

C-3: Polyoxyethylene alkyl ether (EMULGEN 147, manufactured by Kao Corporation)

TABLE 1

| | Component A | Component B | Component C | (A + B)/C (mass) | A/B (mass) | A + B + C Total concentration (% by mass) | Water (% by mass) | Total (% by mass) | Viscosity (mPa·s) | Foam particle size Immediately after stirring (μm) | Evaluation | 5 Minutes after stirring (μm) | Evaluation | 1 Hour after stirring (μm) | Evaluation |
|---|---|---|---|---|---|---|---|---|---|---|---|---|---|---|---|
| Example 1 | A-1 | B-1 | C-1 | 70/30 | 95/5 | 30 | 70 | 100 | 112 | 86 | 5 | 121 | 4 | 156 | 4 |
| | | | | | | 40 | 60 | 100 | 321 | 157 | 4 | 112 | 4 | 234 | 4 |
| | | | | | | 50 | 50 | 100 | 363 | 122 | 4 | 123 | 4 | 175 | 4 |
| | | | | | | 60 | 40 | 100 | 1403 | 58 | 5 | 78 | 5 | 101 | 4 |
| | | | | | | 70 | 30 | 100 | 775 | 42 | 5 | 71 | 5 | 272 | 4 |
| | | | | | | 80 | 20 | 100 | 1668 | 33 | 5 | 27 | 5 | 73 | 5 |
| Example 2 | A-1 | B-1 | C-1 | 35/65 | 95/5 | 30 | 70 | 100 | 50 | 127 | 4 | 148 | 4 | 214 | 4 |
| | | | | | | 40 | 60 | 100 | 442 | 38 | 5 | 143 | 4 | 252 | 4 |
| | | | | | | 50 | 50 | 100 | 509 | 92 | 5 | 107 | 4 | 147 | 4 |
| | | | | | | 60 | 40 | 100 | 397 | 93 | 5 | 127 | 4 | 173 | 4 |
| | | | | | | 70 | 30 | 100 | 358 | 54 | 5 | 76 | 5 | 207 | 4 |
| | | | | | | 80 | 20 | 100 | 448 | 71 | 5 | 60 | 5 | 96 | 5 |
| Example 3 | A-1 | B-1 | C-1 | 70/30 | 50/50 | 30 | 70 | 100 | 74 | 82 | 5 | 118 | 4 | 286 | 4 |
| | | | | | | 40 | 60 | 100 | 1670 | 84 | 5 | 81 | 5 | 192 | 4 |
| | | | | | | 50 | 50 | 100 | 689 | 67 | 5 | 80 | 5 | 185 | 4 |
| | | | | | | 60 | 40 | 100 | 510 | 65 | 5 | 80 | 5 | 113 | 4 |
| | | | | | | 70 | 30 | 100 | 941 | 40 | 5 | 44 | 5 | 68 | 5 |
| | | | | | | 80 | 20 | 100 | 1323 | 37 | 5 | 57 | 5 | 196 | 4 |
| Example 4 | A-1 | B-1 | C-1 | 30/70 | 50/50 | 30 | 70 | 100 | 55 | 143 | 4 | 130 | 4 | 329 | 4 |
| | | | | | | 40 | 60 | 100 | 249 | 105 | 4 | 195 | 4 | 120 | 4 |
| | | | | | | 50 | 50 | 100 | 850 | 66 | 5 | 98 | 5 | 170 | 4 |
| | | | | | | 60 | 40 | 100 | 478 | 39 | 5 | 64 | 5 | 191 | 4 |
| | | | | | | 70 | 30 | 100 | 504 | 60 | 5 | 94 | 5 | 107 | 4 |
| | | | | | | 80 | 20 | 100 | 427 | 114 | 4 | 92 | 5 | 118 | 4 |

TABLE 1-continued

| | Component A | Component B | Component C | (A+B)/C (mass) | A/B (mass) | A+B+C Total concentration (% by mass) | Water (% by mass) | Total (% by mass) | Viscosity (mPa·s) | Foam particle size Immediately after stirring (μm) | Evaluation | 5 Minutes after stirring (μm) | Evaluation | 1 Hour after stirring (μm) | Evaluation |
|---|---|---|---|---|---|---|---|---|---|---|---|---|---|---|---|
| Example 5 | A-1 | B-1 | C-2 | 70/30 | 95/5 | 60 | 40 | 100 | 1140 | 32 | 5 | 72 | 5 | 114 | 4 |
| Example 6 | A-1 | B-1 | C-3 | 70/30 | 95/5 | 80 | 20 | 100 | 1150 | 34 | 5 | 53 | 5 | 85 | 5 |
| Example 7 | A-2 | B-1 | C-1 | 70/30 | 95/5 | 30 | 70 | 100 | 36 | 79 | 5 | 131 | 4 | 373 | 4 |
| | | | | | | 40 | 60 | 100 | 349 | 68 | 5 | 87 | 5 | 132 | 4 |
| | | | | | | 50 | 50 | 100 | 990 | 59 | 5 | 125 | 4 | 201 | 4 |
| | | | | | | 60 | 40 | 100 | 1018 | 52 | 5 | 57 | 5 | 100 | 4 |
| | | | | | | 70 | 30 | 100 | 806 | 26 | 5 | 60 | 5 | 84 | 5 |
| | | | | | | 80 | 20 | 100 | 2595 | 36 | 5 | 70 | 5 | 68 | 5 |
| Example 8 | A-2 | B-1 | C-1 | 50/50 | 95/5 | 30 | 70 | 100 | 45 | 158 | 4 | 200 | 4 | 566 | 3 |
| | | | | | | 40 | 60 | 100 | 246 | 101 | 4 | 173 | 4 | 138 | 4 |
| | | | | | | 50 | 50 | 100 | 1050 | 43 | 5 | 91 | 5 | 142 | 4 |
| | | | | | | 60 | 40 | 100 | 552 | 46 | 5 | 82 | 5 | 126 | 4 |
| | | | | | | 70 | 30 | 100 | 1022 | 46 | 5 | 65 | 5 | 157 | 4 |
| | | | | | | 80 | 20 | 100 | 960 | 21 | 5 | 36 | 5 | 68 | 5 |
| Example 9 | A-2 | B-1 | C-1 | 30/70 | 50/50 | 30 | 70 | 100 | 67 | 188 | 4 | 126 | 4 | 591 | 3 |
| | | | | | | 40 | 60 | 100 | 199 | 99 | 3 | 110 | 4 | 126 | 4 |
| | | | | | | 50 | 50 | 100 | 609 | 83 | 5 | 109 | 4 | 135 | 4 |
| | | | | | | 60 | 40 | 100 | 491 | 90 | 5 | 93 | 5 | 154 | 4 |
| | | | | | | 70 | 30 | 100 | 664 | 92 | 5 | 86 | 5 | 207 | 4 |
| | | | | | | 80 | 20 | 100 | 439 | 92 | 5 | 89 | 5 | 288 | 4 |
| Example 10 | A-2 | B-2 | C-1 | 70/30 | 95/5 | 30 | 70 | 100 | 41 | 84 | 5 | 150 | 4 | 637 | 3 |
| | | | | | | 40 | 60 | 100 | 328 | 110 | 4 | 124 | 4 | 178 | 4 |
| | | | | | | 50 | 50 | 100 | 919 | 43 | 5 | 126 | 4 | 104 | 4 |
| | | | | | | 60 | 40 | 100 | 694 | 78 | 5 | 72 | 5 | 103 | 4 |
| | | | | | | 70 | 30 | 100 | 1191 | 75 | 5 | 51 | 5 | 86 | 5 |
| | | | | | | 80 | 20 | 100 | 1795 | 22 | 5 | 30 | 5 | 70 | 5 |
| Example 11 | A-2 | B-2 | C-1 | 50/50 | 95/5 | 30 | 70 | 100 | 42 | 78 | 5 | 140 | 4 | 997 | 3 |
| | | | | | | 40 | 60 | 100 | 295 | 67 | 5 | 97 | 5 | 402 | 4 |
| | | | | | | 50 | 50 | 100 | 1001 | 70 | 5 | 109 | 4 | 182 | 4 |
| | | | | | | 60 | 40 | 100 | 752 | 55 | 5 | 69 | 5 | 157 | 4 |
| | | | | | | 70 | 30 | 100 | 887 | 41 | 5 | 54 | 5 | 120 | 4 |
| | | | | | | 80 | 20 | 100 | 795 | 27 | 5 | 34 | 5 | 57 | 5 |
| Example 12 | A-2 | B-2 | C-1 | 30/70 | 95/5 | 30 | 70 | 100 | 67 | 115 | 4 | 262 | 4 | 530 | 3 |
| | | | | | | 40 | 60 | 100 | 209 | 88 | 5 | 179 | 4 | 413 | 4 |
| | | | | | | 50 | 50 | 100 | 588 | 88 | 5 | 70 | 5 | 290 | 4 |
| | | | | | | 60 | 40 | 100 | 632 | 65 | 5 | 80 | 5 | 211 | 4 |
| | | | | | | 70 | 30 | 100 | 454 | 84 | 5 | 87 | 5 | 351 | 4 |
| | | | | | | 80 | 20 | 100 | 420 | 49 | 5 | 69 | 5 | 149 | 4 |
| Example 13 | A-2 | B-3 | C-1 | 50/50 | 95/5 | 30 | 70 | 100 | 67 | 98 | 5 | 184 | 4 | 203 | 4 |
| | | | | | | 40 | 60 | 100 | 310 | 114 | 4 | 143 | 4 | 199 | 4 |
| | | | | | | 50 | 50 | 100 | 829 | 76 | 5 | 101 | 4 | 144 | 4 |
| | | | | | | 60 | 40 | 100 | 533 | 44 | 5 | 130 | 4 | 135 | 4 |
| | | | | | | 70 | 30 | 100 | 830 | 54 | 5 | 60 | 5 | 110 | 4 |
| | | | | | | 80 | 20 | 100 | 613 | 38 | 5 | 37 | 5 | 89 | 5 |
| Comparative Example 1 | A-1 | — | — | 100/0 | 100/0 | 80 | 20 | 100 | No fluidity | x | 1 | x | 1 | x | 1 |
| Comparative Example 2 | — | B-1 | — | 100/0 | 0/100 | 10 | 90 | 100 | 2 | 323 | 4 | 672 | 3 | 1339 | 2 |
| | | | | | | 25.5 | 74.5 | 100 | 1235 | x | 1 | x | 1 | x | 1 |
| | | | | | | 40 | 60 | 100 | No fluidity | x | 1 | x | 1 | x | 1 |
| | | | | | | 50 | 50 | 100 | | x | 1 | x | 1 | x | 1 |
| | | | | | | 60 | 40 | 100 | | x | 1 | x | 1 | x | 1 |
| Comparative Example 3 | — | — | C-1 | 0/100 | — | 40 | 60 | 100 | No fluidity | x | 1 | x | 1 | x | 1 |
| | | | | | | 50 | 50 | 100 | | x | 1 | x | 1 | x | 1 |
| | | | | | | 60 | 40 | 100 | | x | 1 | x | 1 | x | 1 |
| Comparative Example 4 | A-2 | — | — | 100/0 | 100/0 | 40 | 60 | 100 | No fluidity | x | 1 | x | 1 | x | 1 |
| | | | | | | 50 | 50 | 100 | No fluidity | x | 1 | x | 1 | x | 1 |
| | | | | | | 60 | 40 | 100 | No fluidity | x | 1 | x | 1 | x | 1 |
| | | | | | | 70 | 30 | 100 | 11441.4 | a | 1 | x | 1 | x | 1 |
| | | | | | | 80 | 20 | 100 | No fluidity | x | 1 | x | 1 | x | 1 |
| Comparative Example 5 | A-1 | B-1 | — | — | 50/50 | 80 | 20 | 100 | No fluidity | x | 1 | x | 1 | x | 1 |
| Comparative Example 6 | — | B-1 | C-1 | 50/50 | — | 50 | 50 | 100 | No fluidity | x | 1 | x | 1 | x | 1 |
| Comparative Example 7 | A-1 | B-1 | C-1 | 30/70 | 40/60 | 60 | 40 | 100 | No fluidity | x | 1 | x | 1 | x | 1 |

TABLE 1-continued

| | Component A | Component B | Component C | (A + B)/C (mass) | A/B (mass) | A + B + C Total concentration (% by mass) | Water (% by mass) | Total (% by mass) | Viscosity (mPa·s) | Immediately after stirring (μm) | Evaluation | 5 Minutes after stirring (μm) | Evaluation | 1 Hour after stirring (μm) | Evaluation |
|---|---|---|---|---|---|---|---|---|---|---|---|---|---|---|---|
| Comparative Example 8 | A-2 | B-1 | C-1 | 90/10 | 50/50 | 50 | 50 | 100 | No fluidity | x | 1 | x | 1 | x | 1 |
| Comparative Example 9 | A-2 | B-1 | C-1 | 10/90 | 50/50 | 50 | 50 | 100 | No fluidity | x | 1 | x | 1 | x | 1 |

TABLE 2

| | Component A | Component B | Component C | (A + B)/C (mass) | A/B (mass) | A + B + C Total concentration (% by mass) | Water (% by mass) | Total (% by mass) | Viscosity (mPa·s) | Immediately after stirring (μm) | Evaluation | 5 Minutes after stirring (μm) | Evaluation | 1 Hour after stirring (μm) | Evaluation |
|---|---|---|---|---|---|---|---|---|---|---|---|---|---|---|---|
| Example 14 | A-3 | B-4 | C-1 | 60/40 | 85/15 | 65 | 35 | 100 | 452 | 46 | 5 | 75 | 5 | 84 | 5 |
| Example 15 | | B-5 | | | | | | | 1087 | 59 | 5 | 51 | 5 | 71 | 5 |
| Example 16 | | B-6 | | | | | | | 655 | 34 | 5 | 47 | 5 | 81 | 5 |
| Example 17 | | B-7 | | | | | | | 1084 | 38 | 5 | 46 | 5 | 77 | 5 |
| Example 18 | | B-8 | | | | | | | 847 | 41 | 5 | 92 | 5 | 69 | 5 |

TABLE 3

| | Component A | HAS/IOS in component A (Mass) | Component B | Component C | (A + B)/C (mass) | A/B (mass) | A + B + C Total concentration (% by mass) | Water (% by mass) | Total (% by mass) | Viscosity (mPa·s) | Immediately after stirring (μm) | Evaluation | 5 Minutes after stirring (μm) | Evaluation | 1 Hour after stirring (μm) | Evaluation |
|---|---|---|---|---|---|---|---|---|---|---|---|---|---|---|---|---|
| Example 19 | Mixture of A-3 and A-4 | 84/16 | B-1 | C-1 | 60/40 | 95/5 | 70 | 30 | 100 | 785 | 31 | 5 | 57 | 5 | 74 | 5 |
| Example 20 | | 75/25 | | | | | | | | 1471 | 27 | 5 | 38 | 5 | 71 | 5 |
| Example 21 | | 65/35 | | | | | | | | 841 | 40 | 5 | 45 | 5 | 53 | 5 |
| Example 22 | | 55/45 | | | | | | | | 930 | 35 | 5 | 53 | 5 | 58 | 5 |

It is understood from Tables 1 to 3 that the surfactant compositions of Examples 1 to 22 have fluidity and low viscosity over a wide concentration range. In addition, the surfactant compositions of Examples 1 to 22 even at a high concentration give fine foam, and the composition sustains a fine foam state for a long time after foaming. On the other hand, it is understood that the surfactant compositions of Comparative Examples 1 to 9 have high viscosity and no fluidity at high concentrations. In addition, it is understood that the surfactant compositions of Comparative Examples 1 to 9 do not foam at all even when they are stirred.

INDUSTRIAL APPLICABILITY

The surfactant composition of the present invention is useful as a detergent for various uses.

The invention claimed is:
1. A surfactant composition comprising component A, component B, component C, and component D described below,
wherein
a total content of the component A, the component B and the component C is 45% by mass or more and 80% by mass or less;
a mass ratio (A+B)/C of a total content of the component A and the component B to a content of the component C is from 20/80 to 80/20; and
a mass ratio A/B of a content of the component A to a content of the component B is from 98/2 to 45/55,
A: an internal olefin sulfonic acid having 12 to 24 carbon atoms and/or a salt thereof;
B: an anionic surfactant other than the component A, wherein said anionic surfactant is at least one member from the group consisting of a sulfuric acid ester salt having 10 to 22 carbon atoms, a sulfonate having 10 to 22 carbon atoms, a fatty acid salt having 10 to 22 carbon atoms, a carboxylate having 10 to 22 carbon atoms, a phosphoric acid ester salt having 10 to 22 carbon atoms, and an amino acid salt having an acyl group having 10 to 22 carbon atoms;

C: a nonionic surfactant which is at least one member selected from the group consisting of a polyalkylene glycol nonionic surfactant, a polyhydric alcohol nonionic surfactant, and a fatty acid alkanol amide; and D: water, wherein a viscosity measured by a tuning fork vibrational viscometer at 25° C. is 3000 mPa·s or less.

2. The surfactant composition according to claim 1, wherein the internal olefin sulfonic acid and/or the salt thereof contains 5% by mass or more and 40% by mass or less of an internal olefin sulfonic acid/or a salt thereof having a sulfonic acid group at 2-position.

3. The surfactant composition according to claim 1, wherein the internal olefin sulfonate includes a hydroxyalkane sulfonate (HAS) and an olefin sulfonate (IOS).

4. The surfactant composition according to claim 1, which is a detergent.

5. A cleaning method using the surfactant composition according to claim 1.

6. The surfactant composition according to claim 2, wherein the internal olefin sulfonate includes a hydroxyalkane sulfonate (HAS) and an olefin sulfonate (IOS).

* * * * *